US011291794B2

(12) United States Patent
Acker et al.

(10) Patent No.: US 11,291,794 B2
(45) Date of Patent: Apr. 5, 2022

(54) COMPENSATING FOR DISRUPTIONS IN BREATHING GAS FLOW MEASUREMENT

(71) Applicant: Mallinckrodt Pharmaceuticals Ireland Limited, Dublin (IE)

(72) Inventors: Jaron M. Acker, Madison, WI (US); Craig R. Tolmie, Stoughton, WI (US)

(73) Assignee: Mallinckrodt Pharmaceuticals Ireland Limited, Dublin (IE)

( * ) Notice: Subject to any disclaimer, the term of this patent is extended or adjusted under 35 U.S.C. 154(b) by 240 days.

(21) Appl. No.: 16/598,786

(22) Filed: Oct. 10, 2019

(65) Prior Publication Data

US 2020/0114111 A1  Apr. 16, 2020

Related U.S. Application Data

(63) Continuation of application No. 15/420,689, filed on Jan. 31, 2017, now Pat. No. 10,478,584.

(Continued)

(51) Int. Cl.
*A61M 16/12* (2006.01)
*A61M 16/00* (2006.01)
*A61M 16/10* (2006.01)

(52) U.S. Cl.
CPC ...... *A61M 16/125* (2014.02); *A61M 16/0051* (2013.01); *A61M 16/0069* (2014.02); *A61M 16/024* (2017.08); *A61M 16/104* (2013.01); *A61M 2016/0033* (2013.01); *A61M 2016/0039* (2013.01); *A61M 2016/1025* (2013.01);
(Continued)

(58) Field of Classification Search
CPC .............. A61M 16/0051; A61M 16/12; A61M 16/0069; A61M 16/0057; A61M 16/00; A61M 16/024; A61M 16/104; A61M 16/205; A61M 16/01; A61M 16/026; A61M 16/0003; A61M 16/202; A61M 16/1005; A61M 16/0063; A61M 16/0066; A61M 16/0081; A61M 16/16; A61M 16/0677; A61M 16/122; A61M 16/20; A61K 33/00; G06F 19/3481

See application file for complete search history.

(56) References Cited

U.S. PATENT DOCUMENTS 5,558,083 A  9/1996 Bathe et al.
5,732,693 A  3/1998 Bathe et al.
(Continued)

FOREIGN PATENT DOCUMENTS

WO  0195972 A2  12/2001

OTHER PUBLICATIONS

Extended European Search Report for Application No. EP17748014.2, dated Aug. 16, 2019, 10 Pages.
(Continued)

*Primary Examiner* — Manuel A Mendez

(57) ABSTRACT

The present disclosure generally relates to systems and methods for delivery of therapeutic gas to patients, using techniques to compensate for disruptions in breathing gas flow measurement, such as when breathing gas flow measurement is unavailable or unreliable. Such techniques include using historical breathing gas flow rate data, such as moving average flow rates, moving median flow rates and/or flow waveforms. At least some of these techniques can be used to ensure that interruption in therapeutic gas delivery is minimized or eliminated.

21 Claims, 5 Drawing Sheets

Related U.S. Application Data

(60) Provisional application No. 62/290,430, filed on Feb. 2, 2016.

(52) U.S. Cl.
CPC ............ *A61M 2016/1035* (2013.01); *A61M 2202/0275* (2013.01); *A61M 2205/3334* (2013.01); *A61M 2205/52* (2013.01); *A61M 2230/435* (2013.01); *A61M 2230/437* (2013.01)

(56) References Cited

U.S. PATENT DOCUMENTS

| | | |
|---|---|---|
| 6,089,229 A | 7/2000 | Bathe et al. |
| 6,125,846 A | 10/2000 | Bathe et al. |
| 7,159,608 B1 | 1/2007 | Lucas, Jr. et al. |
| 7,523,752 B2 | 4/2009 | Montgomery et al. |
| 8,282,966 B2 | 10/2012 | Baldassarre et al. |
| 8,291,904 B2 | 10/2012 | Bathe et al. |
| 8,293,284 B2 | 10/2012 | Baldassarre et al. |
| 8,431,163 B2 | 4/2013 | Baldassarre et al. |
| 8,573,209 B2 | 11/2013 | Bathe et al. |
| 8,573,210 B2 | 11/2013 | Bathe et al. |
| 8,776,794 B2 | 7/2014 | Bathe et al. |
| 8,776,795 B2 | 7/2014 | Bathe et al. |
| 8,795,741 B2 | 8/2014 | Baldassarre |
| 8,846,112 B2 | 9/2014 | Baldassarre |
| 2003/0189492 A1 | 10/2003 | Harvie |
| 2008/0053441 A1 | 3/2008 | Gottlib et al. |
| 2009/0314290 A1 | 12/2009 | Hickle |
| 2010/0224192 A1 | 9/2010 | Dixon et al. |
| 2012/0080103 A1 | 4/2012 | Levine et al. |
| 2014/0048063 A1 | 2/2014 | Bathe et al. |
| 2014/0261410 A1 | 9/2014 | Sanchez et al. |
| 2015/0233879 A1* | 8/2015 | Tolmie ............... G01N 33/0037 128/202.22 |
| 2015/0314101 A1* | 11/2015 | Acker ................. A61M 16/024 128/203.14 |
| 2015/0320952 A1* | 11/2015 | Acker ................. A61M 16/202 128/202.22 |

OTHER PUBLICATIONS

INOblender Operations Manual, Ikaria, Inc. 2010, 34 pages.
INOmax DSIR (Delivery System): Operation Manual (800 ppm INOMAX (nitric oxide) for Inhalation), Ikaria, Inc. 2012, 136 pages.
INOmax DS.sub.IR INOblender—Pre-Use Checkout, Ikaria, Inc. 2014, 2 pages.
INOmax Label, Nitric Oxide Gas, INO Therapeutics 2013, 2 pages.
INOvent Delivery System: Operation and Maintenance Manual (CGA Variant), Datex-Ohmeda, Inc. 2000, 180 pages.
International Preliminary Report on Patentability for International PCT Patent Application No. PCT/US2017/015825, dated Aug. 16, 2018, 10 pages.
International Search Report and Written Opinion for International Application No. PCT/US2017/015825, dated Apr. 17, 2017, 11 Pages.
Using the INOpulse DS Subject Guide, Ikaria, Inc. 2012, 50 pages.

* cited by examiner

COMPENSATING FOR DISRUPTIONS IN BREATHING GAS FLOW MEASUREMENT

CROSS-REFERENCE TO RELATED APPLICATION

This application is a continuation of U.S. application Ser. No. 15/420,689, filed on Jan. 31, 2017 which claims priority to U.S. provisional application No. 62/290,430, filed on Feb. 2, 2016, the contents of which are incorporated herein by reference in their entirety.

FIELD

The present disclosure generally relates to delivery of therapeutic gas to patients.

BACKGROUND

Therapeutic gas can be delivered to patients, to provide medical benefits. One such therapeutic gas is nitric oxide (NO) gas that, when inhaled, acts to dilate blood vessels in the lungs, improving oxygenation of the blood and reducing pulmonary hypertension. Because of this, nitric oxide can be provided as a therapeutic gas in the inspiratory breathing gases for patients with pulmonary hypertension.

Many of these patients who may benefit from nitric oxide gas receive breathing gas from a breathing circuit affiliated with a ventilator (e.g., constant flow ventilator, variable flow ventilator, high frequency ventilator, bi-level positive airway pressure ventilator or Bi PAP ventilator, etc.). To provide nitric oxide to a patient who receives breathing gas from a ventilator, nitric oxide may be injected into the breathing gas flowing in the breathing circuit. This inhaled nitric oxide (iNO) is often provided as a constant concentration, which is provided based on proportional delivery of the NO to the breathing gas.

Although the above provides many benefits, there remains a need for improvements to delivery of therapeutic gas. For example, there remains a need for new techniques to at least address situations such as, but not limited to, disruptions in breathing gas flow systems used in the delivery of therapeutic gases such as nitric oxide.

SUMMARY

Aspects of the present disclosure relate to therapeutic gas delivery systems (e.g., nitric oxide delivery systems) that utilize new techniques for compensating for errors or disruptions in breathing gas flow measurement. In some examples, the therapeutic gas delivery systems disclosed herein store historical breathing gas flow rate data (e.g. average breathing gas flow, breathing gas flow waveforms, etc.) and can use this historical breathing gas flow rate data when current breathing gas flow rate data is unavailable or unreliable. As a result, such exemplary therapeutic gas delivery systems can continue to provide therapeutic gas delivery without any significant interruption in treatment.

In an example of an implementation, there is provided a therapeutic gas delivery apparatus, the apparatus comprising: a therapeutic gas injector module configured to be placed in fluid communication with a breathing circuit affiliated with the ventilator, the therapeutic gas injector module including a breathing gas flow inlet, a therapeutic gas flow inlet, and a combined breathing gas and therapeutic gas flow outlet for providing a combined flow of breathing gas and therapeutic gas to a patient, in need thereof; a first flow sensor configured to sense breathing gas flow rate data; and a controller configured to control the delivery flow rate of the breathing gas based on a first mode, and upon detection of a disruption, configured to control delivery flow of the breathing gas based on the historical breathing gas flow rate data previously sensed by the first flow sensor and stored in the memory.

The controller may comprise a memory configured to store historical flow rate data related to the sensed breathing gas flow rate data by the first flow sensor; and a detection processor configured to detect a disruption of the sensed breathing gas flow rate data from the first flow sensor, wherein the first flow sensor is a gas inspiratory flow sensor, and the controller is configured to use the historical breathing gas flow rate based on a historical average upon detection of a disruption in the form of a failure of an operation of a gas inspiratory flow sensor. The historical flow rate data may include one or more of a moving average breathing gas flow rate, a moving median breathing gas flow rate, and/or a gas flow rate waveform. The historical flow rate data may be stored over a period in the range from 10 seconds to 5 minutes. The sensed breathing gas flow rate may be received from the injector module. The sensed breathing gas flow rate may be received from the ventilator. The sensed breathing gas flow rate data may comprise first breathing gas flow rate data, and second breathing gas flow rate data, and wherein the first breathing second gas flow rate data is received from the injector module and the second breathing gas flow rate data is received from the ventilator. The controller may compare respective flow rate data from the first breathing gas flow rate data with the second breathing gas flow rate data. The controller may be configured to automatically resume delivery of a flow of breathing gas based on the first mode, upon detection and/or input that the first flow sensor has been one of reconnected, replaced and/or serviced. The controller may be further configured to utilize at least one of data smoothing and/or low-pass filtering to remove outlying stored flow data points.

In another example of an implementation, a method is provided for delivery of therapeutic gas to a patient, the method comprising: controlling via a controller breathing gas flow to a patient in a first mode; receiving sensed flow rate data of the breathing gas flow; storing in a memory historical flow rate data related to the received breathing gas flow rate data by the sensor; detecting a disruption of the sensed breathing gas flow rate data from the sensor; and controlling via the controller the breathing gas flow in a temporary mode instead of the first mode, based on the received breathing gas flow rate data.

The historical sensed flow rate data may comprise one or more of a moving average breathing gas flow rate, a moving median breathing gas flow rate, and/or a gas flow rate waveform. Storing the historical flow data may include storing the historical flow rate data over a period in the range from 10 seconds to 5 minutes. The method may further comprise returning to the first mode when a discontinuance of the disruption is detected. Receiving the received flow rate data includes receiving a first received flow rate data and a second received flow rate data from, and detecting the disruption includes detecting the disruption by comparing respective flow rate data between the two or more received flow rate data groups.

In another example of an implementation, an apparatus for delivery of nitric oxide and therapeutic gas to a patient is provided, comprising: a controller configured to control gas flow to a patient in a first mode and to receive sensed flow rate data; a receiver configured to receive sensed flow rate data of the breathing gas flow; a memory configured to store received breathing gas flow rate data related to previous sensed historical flow data; a detector configured to detect a disruption of received breathing gas flow rate data from the received breathing gas flow rate data; and wherein the controller is further configured to retrieve historical flow rate data, and to control breathing gas flow rate in a temporary mode, instead of the first mode, based on the historical flow rate.

The historical sensed flow rate data may comprise one or more of a moving average breathing gas flow rate, a moving median breathing gas flow rate, and/or a breathing gas flow waveform. The historical flow rate data may be stored over a period in the range from 10 seconds to 5 minutes. The controller may be further configured return to the first mode when a discontinuance of the disruption is detected. The received sensed flow rate data may comprise a first received flow rate data and a second received flow rate data from two or more sensors, and detecting the disruption may include comparing flow rate data between the two or more received flow rate data.

Other features and aspects will be apparent from the following detailed description, the drawings, and the claims.

BRIEF DESCRIPTION OF THE DRAWINGS

The features and advantages of the present description will be more fully understood with reference to the following, detailed description when taken in conjunction with the accompanying figures, wherein.

DETAILED DESCRIPTION

Figure 1:
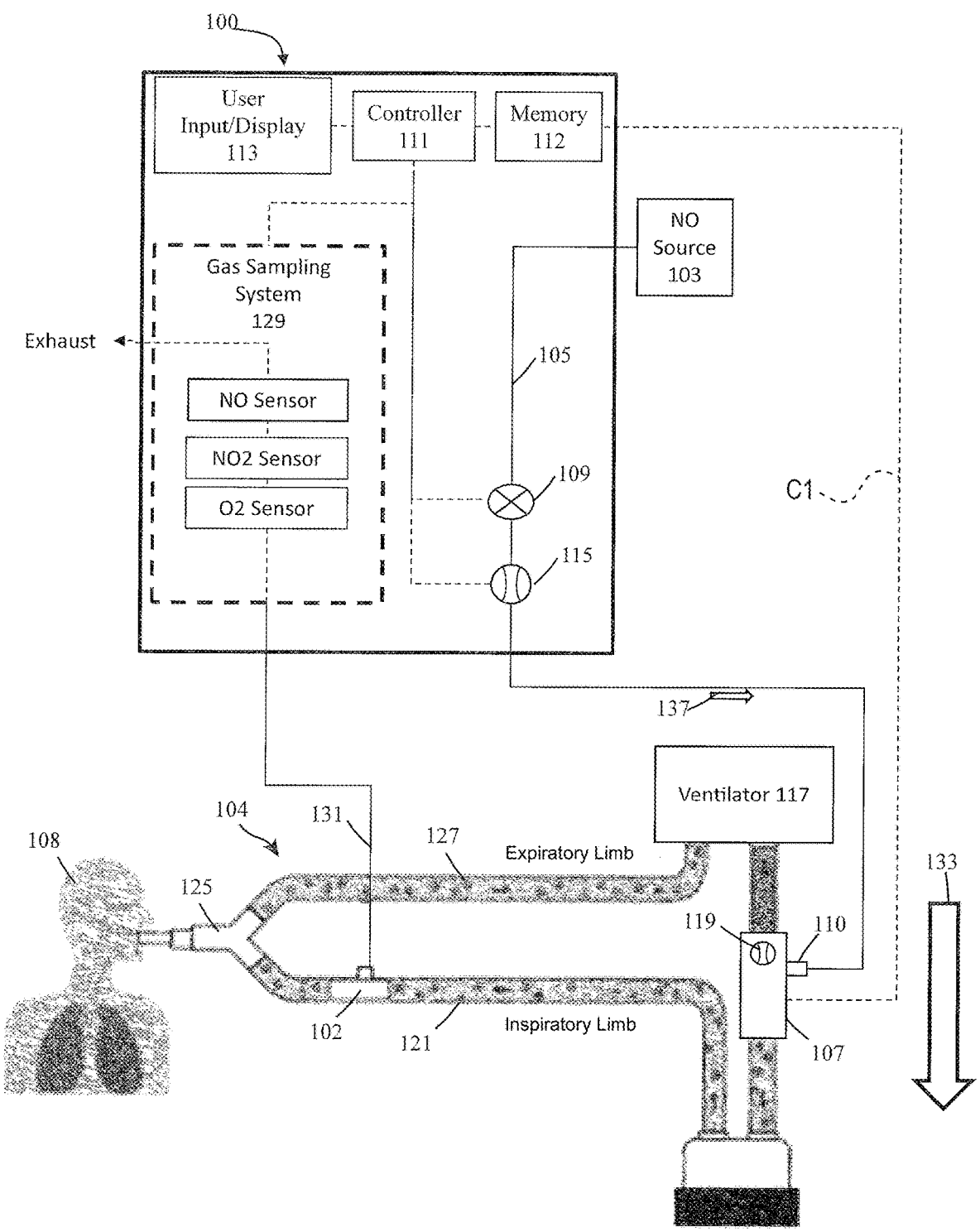
FIG. 1 illustratively depicts an exemplary nitric oxide delivery system having a flow sensor in a breathing circuit, in accordance with exemplary descriptions of the present description.

The present disclosure generally relates, to systems and methods for delivery of therapeutic gas to patients (e.g., patients receiving breathing gas, which can include therapeutic gas, from a ventilator via a breathing circuit) using previously unknown techniques to compensate for disruptions in breathing gas flow measurement, for example, such as when breathing gas flow measurement is unavailable or unreliable. Such techniques can include, but are not limited to, using historical breathing gas flow rate data, such as moving average flow rates, moving median flow rates, integrations of flow over a known time period for determining gas volume, and/or flow waveforms, to name a few. At least some of these techniques can be used to mitigate interruption in therapeutic gas delivery and/or ensure that there is no interruption in therapeutic gas delivery. Reducing and/or eliminating interruption of therapeutic gas being delivered to a patient in need thereof can, amongst other things, improve patient safety (e.g., reducing and/or eliminating the risk of rebound pulmonary hypertension, reducing and/or eliminating incorrect dosing, etc.).

Systems and methods described herein can deliver therapeutic gas to a patient from a delivery system to an injector module, which in turn can be in fluid communication with a breathing circuit (affiliated with a ventilator) that the patient receives breathing gas from. These systems and methods can include at least one breathing gas flow sensor that can measure the flow of patient breathing gas in the breathing circuit. Further, systems and methods described herein can deliver therapeutic gas into the breathing circuit such that the therapeutic gas wild stream blends with the patient breathing gas. Advantageously, the therapeutic gas delivery system and methods described herein can store past breathing gas flow measurement for use in the event of a disruption in breathing gas flow measurement.

The term "disruption" is used herein to encompass any and all of various types of disruptions. For example, the term "fault" is, at times, used herein to refer to any type of disruption. For example, one exemplary type of disruption may occur when a gas sensor becomes decoupled from, and/or loses electrical communication with, a control module affiliated with an exemplary nitric oxide delivery system. Another exemplary type of disruption, in the case of multiple sensors, is when one or more sensors provide inaccurate or mismatched readings. Yet another exemplary type of disruption may be when readings from a sensor are recognized by the controller as deviating from normal, expected, and/or desired ranges, which may include, for example, a partial or total cessation of received sensor data that they are likely inaccurate. Another exemplary type of disruption is when the sensor itself or other components related to delivery of breathing gas may indicate a failed or disconnected state. Depending partially on the system location of a sensor, it may be subject to some wear and tear (e.g., by being bumped against surrounding objects). For example wear and tear may occur when the sensor is closer to the remote patient end of the gas flow pathway, for example by the sensor being located at an injector module component, which in turn can be coupled to and/or in fluid communication with the patient breathing circuit. Many types of disruptions or faults can occur; however, merely for the sake of ease, all types of disruptions are not described herein, but will be understood to those skilled in the art. At least some of the systems and methods described herein can be used to prevent interruption of therapeutic gas delivery when a disruption occurs.

Referring to FIG. 1, illustratively depicted is an exemplary nitric oxide delivery system 100 for delivering therapeutic nitric oxide gas, via an injector module 102, to a patient 108 receiving breathing gas from a breathing circuit 104 affiliated with a ventilator 117. It will be understood that any teachings of the present description can be used in any applicable system for delivering therapeutic gas to a patient receiving breathing gas from a breathing apparatus (e.g., ventilator, high frequency ventilator, breathing mask, nasal cannula, etc.). For example, systems and methods of the present description can use, modify, and/or be affiliated with the delivery systems and/or other teachings of U.S. Pat. No. 5,558,083 entitled "Nitric Oxide Delivery System", the contents of which is incorporated herein by reference in its entirety.

The disclosure here at times refers to use with a ventilator; however, systems and methods described herein can be used with any applicable breathing apparatus that may be affiliated with ventilation. Accordingly, reference to a ventilator is merely for ease of description and is in no way meant to be a limitation. The therapeutic gas, therapeutic gas wild stream blended into the breathing circuit, therapeutic gas delivery system, and the like are, at times, described with reference to nitric oxide gas (NO, iNO, etc.) used for inhaled nitric oxide gas therapy. It will be understood that other applicable therapeutic gases can be used. Accordingly, reference to nitric oxide, NO, iNO, and the like is merely for ease and is in no way meant to be a limitation.

In exemplary descriptions, exemplary nitric oxide delivery systems such as nitric oxide delivery system 100 can be used to wild stream blend therapeutic gas (e.g., nitric oxide, NO, etc.) into patient breathing gas in a breathing circuit (affiliated with a ventilator) as a proportion of the patient breathing gas. To at least wild stream blend NO into patient breathing gas, nitric oxide delivery system 100 can include and/or receive nitric oxide from a nitric oxide source 103 (e.g., cylinder storing NO, NO generator, etc.) for example, via a conduit 105. Further, conduit 105 can also be in fluid communication with an injector module 102, for example, via a therapeutic gas inlet 110. The injector module 102 can also be in fluid communication with an inspiratory limb 121 of patient breathing circuit 104 affiliated with ventilator 117.

As shown, ventilator 117 can include an inspiratory outlet for delivering breathing gas (e.g., forward flow 133) to the patient via an inspiratory limb 121 and a "Y" piece 125 of a patient breathing circuit and an expiratory inlet for receiving patient expiration via an expiratory limb 127 and "Y" piece 125 of the patient breathing circuit. Generally speaking, this "Y" piece may couple inspiratory limb 121 and expiratory limb 127 and breathing gas being delivered and/or patient expiration may flow through the "Y" piece. At times, for ease, delivery and expiration of breathing gas is described without reference to the "Y" piece. This is merely for ease and is in no way meant to be a limitation.

With injector module 102 coupled to inspiratory limb 121 of the breathing circuit and/or in fluid communication with the breathing circuit, nitric oxide can be delivered from nitric oxide delivery system 100 (e.g., NO forward flow 137) to injector module 102, via conduit 105 and/or therapeutic gas inlet 110. This nitric oxide can then be delivered, via injector module 102, into inspiratory limb 121 of the patient breathing circuit affiliated ventilator 117 being used to delivery breathing gas to a patient 108. In at least some instances, the patient breathing circuit can include only one limb for both inspiratory and expiratory flow. For ease, patient breathing circuits are, at times, depicted as having a separate inspiratory limb and expiratory limb. This is merely for ease and is in no way meant to be a limitation. For example, at times, the present disclosure is described and/or depicted for use with a dual limb (e.g., inspiratory limb and expiratory limb) patient breathing circuit; however, the present disclosure can, when applicable, be used with single limb patient breathing circuit (e.g., only inspiratory limb, combine inspiratory limb and expiratory limb, etc.). Again, this is merely for ease and is in no way meant to be a limitation.

In exemplary embodiments, to regulate flow of nitric oxide through conduit 105 to injector module 102, and in turn to a patient 108 receiving breathing gas from the patient breathing circuit, nitric oxide delivery system 100 can include one or more control valves 109 (e.g., proportional valves, binary valves, etc.). For example, with control valve 109 open, nitric oxide can be delivered to patient 108 by flowing in a forward direction (e.g., NO forward flow 137) through conduit 105 to injector module 102, and in turn to patient 108.

In at least some instances, nitric oxide delivery system 100 can include one or more NO flow sensors 115 that can measure the flow of therapeutic gas (e.g., measure flow through control valve 109, flow through conduit 105, etc.). Flow sensor 115 can be located up stream or downstream from control valve 109 and/or conduit 105, in turn enabling measurement of the flow of therapeutic gas through a therapeutic gas inlet 110 into injector module 102, and in turn to patient 108.

Figure 2:
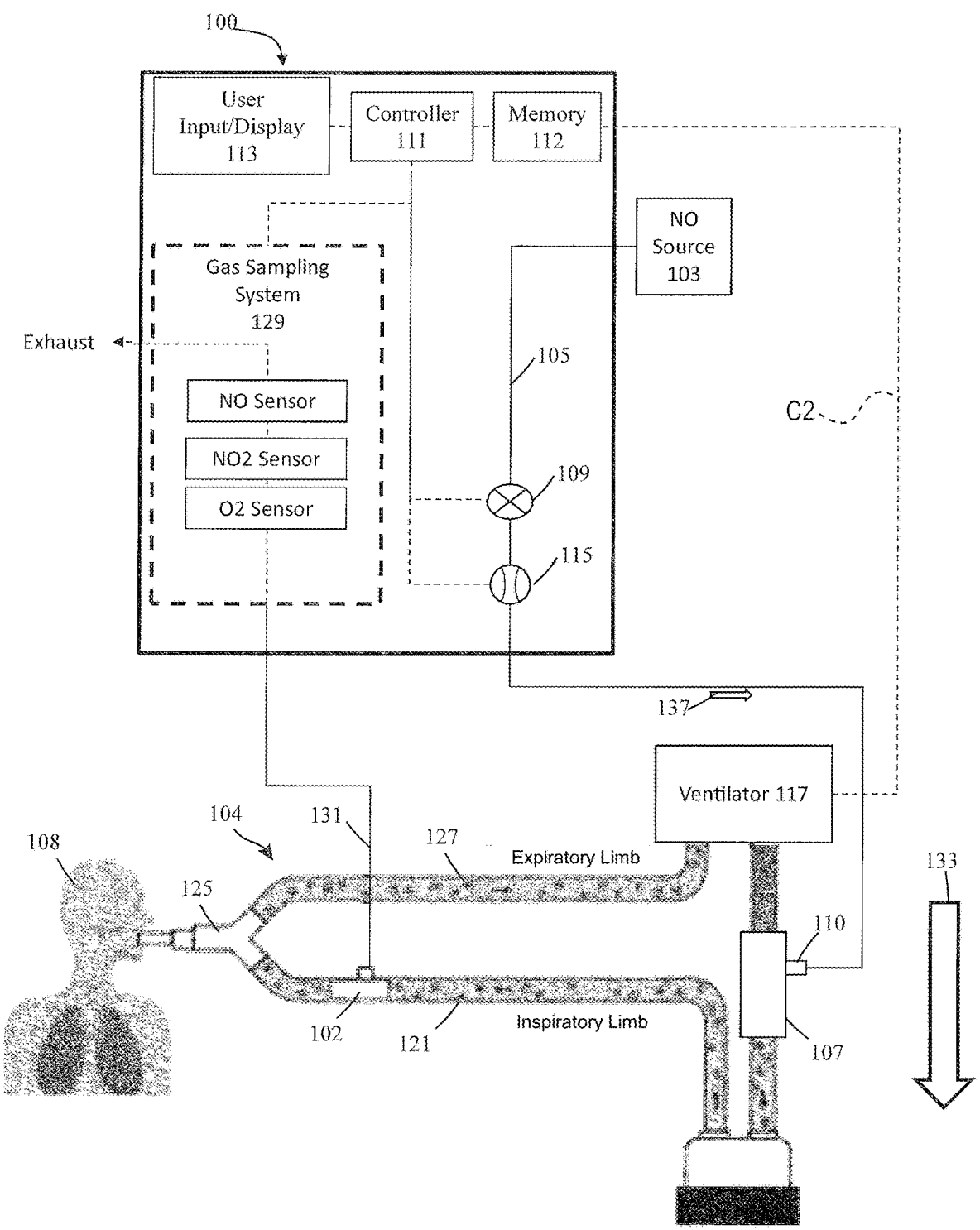
FIG. 2 illustratively depicts an exemplary nitric oxide delivery system in communication with a ventilator, in accordance with exemplary descriptions of the present description.
Figure 3:
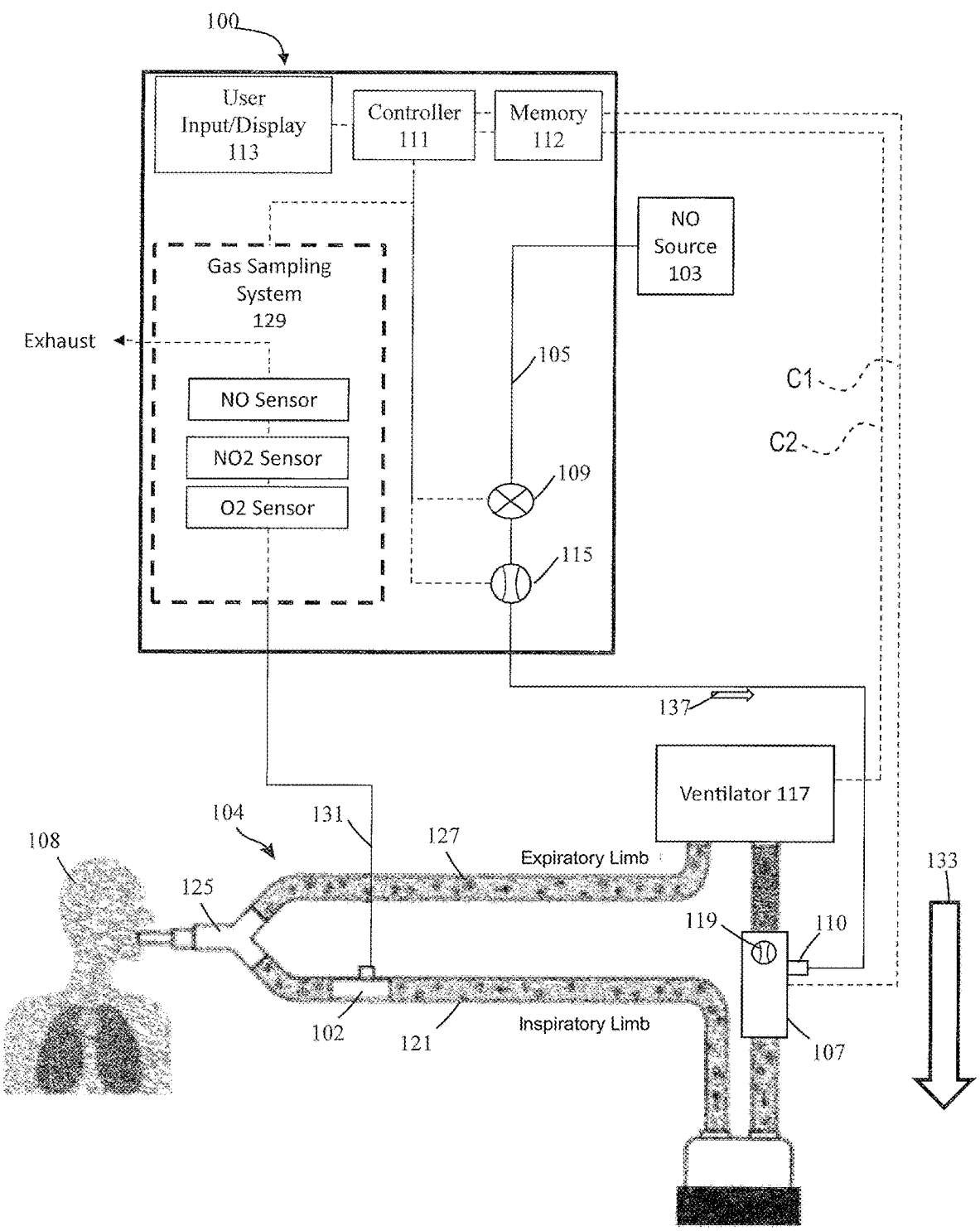
FIG. 3 illustratively depicts an exemplary nitric oxide delivery system having a flow sensor in a breathing circuit and also in communication with a ventilator, in accordance with exemplary descriptions of the present description.

Further, in at least some instances, injector module 102 can include one or more breathing gas flow sensors 119 that can measure the flow of at least patient breathing gas (e.g., forward flow 133) through injector module 102, and in turn to patient 108. In some implementations, there may be sensors (not shown) that sense expiratory flow. Although shown as being at injector module 102, breathing gas flow sensor 119 can be placed elsewhere in the inspiratory limb 121, such as upstream of the injector module 102 and/or in fluid communication with the breathing circuit. Also, as shown in FIG. 2, instead of receiving flow rate data from breathing gas flow sensor 119, in at least some instances, nitric oxide delivery system 100 may receive flow rate data directly from the ventilator 117 indicating the flow of breathing gas from ventilator 117. Further, in at least some instances, flow rate data is provided by both the breathing gas flow sensor 119 and the ventilator 117, as shown in FIG. 3.

Nitric oxide gas flow can be wild stream blended proportional (also known as ratio-metric) with the breathing gas flow to provide a desired concentration of NO in the combined breathing gas and therapeutic gas. For example, nitric oxide delivery system 100 can confirm that the desired concentration of NO is in the combined breathing gas and therapeutic gas by using the known NO concentration of NO source 103; the amount of breathing gas flow in the patient circuit using gas flow rate data from breathing gas flow sensor 119; and the amount of therapeutic gas flow in conduit 105 to injector module 102 (and in turn to patient 108) using gas flow rate data from NO flow sensor 115.

To at least deliver desired set doses of therapeutic gas to a patient and/or sample therapeutic gas being delivered to a patient, therapeutic gas delivery system 100 can include a system controller 111 that may comprise one or more processors and memory 112, where the system controller may be for example a computer system, a single board computer, one or more application-specific integrated circuits (ASICs), or a combination thereof. Processors can be coupled to memory and may be one or more of readily available memory such as random access memory (RAM), read only memory (ROM), flash memory, compact/optical disc storage, hard disk, or any other form of local or remote digital storage. Support circuits can be coupled to processors, to support processors, sensors, valves, sampling systems, delivery systems, user inputs, displays, injector modules, breathing apparatus, etc. in a conventional manner. These circuits can include cache memory, power supplies, clock circuits, input/output circuitry, analog-to-digital and/or digital-to-analog convertors, subsystems, power controllers, signal conditioners, and the like. Processors and/or memory can be in communication with sensors, valves, sampling systems, delivery systems, user inputs, displays, injector modules, breathing apparatus, etc. Communication to and from the system controller may be over a communication path, where the communication path may be wired or wireless, and wherein suitable hardware, firmware, and/or software may be configured to interconnect components and/or provide electrical communications over the communication path(s).

The clock circuits may be internal to the system controller and/or provide a measure of time relative to an initial start, for example on boot-up. The system may comprise a real-time clock (RTC) that provides actual time, which may be synchronized with a time-keeping source, for example a network. The memory 112 may be configured to receive and store values for calculations and/or comparison to other values, for example from sensor(s), pumps, valves, etc.

The memory 112 may store a set of machine-executable instructions (or algorithms), when executed by processors, that can cause the sampling system and/or delivery system to perform various methods and operations. For example, the nitric oxide delivery system can deliver a desired set dose of therapeutic gas (e.g., desired NO concentration, desired NO PPM, etc.) to a patient in need thereof. To this end, the delivery system may receive and/or determine a desired set dose of therapeutic gas to be delivered to a patient, for example, that may be input by a user. The delivery system can measure flow in the inspiratory limb of a patient breathing circuit, and while delivering therapeutic gas containing NO to the patient the system can monitor inspiratory flow or changes in the inspiratory flow. The system can also vary the quantity (e.g. volume or mass) of therapeutic gas delivered in a subsequent inspiratory flow.

In another example, the sampling system can determine the concentration of target gas (e.g., NO) being delivered to a patient. To this end, a sampling pump may be operated and/or a gas sampling valve (e.g., three way valve, etc.) be opened to obtain a gas sample from the inspiratory limb of a patient breathing circuit. The gas sample may include blended air and therapeutic gas (e.g., NO) being delivered to a patient. The gas sample may be exposing to gas sensors (e.g., catalytic type electrochemical gas sensors) to obtain gas flow rate data from the sensor indicative of the concentration of target gas (e.g., NO, nitrogen dioxide, oxygen) being delivered to the patient. The concentration of the target gas may be communicated to a user. The machine-executable instructions may also comprise instructions for any of the other methods described herein.

Further, to at least ensure accurate dosing of the therapeutic gas, nitric oxide delivery system 100 can include a user input/display 113 that can include a display and a keyboard and/or buttons, or may be a touchscreen device. User input/display 113 can receive desired settings from the user, such as the patient's prescription (in mg/kg ideal body weight, mg/kg/hr, mg/kg/breath, mL/breath, cylinder concentration, delivery concentration, duration, etc.), the patient's age, height, sex, weight, etc. User input/display 113 can in at least some instances be used to confirm patient dosing and/or gas measurements, for example, using a gas sampling system 129 that can receive samples of the gas being delivered to patient 108 via a sample line 131. Gas sampling system 129 can include numerous sensors such as, but not limited to, nitric oxide gas sensors, nitrogen dioxide gas sensors, and/or oxygen gas sensors, to name a few that can be used to at least display relevant information (e.g., gas concentrations, etc.) on user input/display 113 and/or provide alerts to the user. The nitric oxide delivery system 100 can thus operate in a first mode by which gas flow is delivered based on desired settings and/or parameters.

FIG. 1 illustrates an example where the system controller 111 is configured to receive sensed data via a communication pathway C1 from the sensor 119 located at injector module 102. The components shown in FIGS. 1-3 disclose similar components with similar reference numbers. Therefore the sake of clarity and brevity, the components common to FIGS. 1-3 are described herein with respect primarily to FIG. 1.

Although the above can be used beneficially to deliver therapeutic gas to a patient that is receiving breathing gas from a patient breathing circuit affiliated with a ventilator, wild stream blending of NO into patient breathing gas as a percentage of the patient breathing gas can fail if the breathing gas flow information is unavailable and/or unreliable.

In exemplary embodiments, at least injector module 102 can be exposed to wear and tear. For example, as shown in FIG. 1, injector module 102 can be exposed to wear and tear as it is a component that is external to the main delivery system 100, and is coupled to the inspiratory limb of the breathing circuit, injector module 102 can also be exposed to disinfecting and/or sterilization processes adding additional wear and tear. The injector module 102 may also be easily dropped, dragged, or placed in the wrong part of the breathing circuit (e.g. downstream of the humidifier or on the exhalation side of the circuit), which can cause additional wear and tear. In summary, injector module 102 and the sensors therein (e.g. breathing gas flow sensor 119, etc.) may be more prone to fault/disruption than other components in the system, for example, at least because of the wear and tear described above.

For nitric oxide delivery systems that are in direct communication with the ventilator (e.g. serial, USB, Ethernet, wireless communication, etc.) inspiratory flow information can be provided by the ventilator instead of or in addition to a breathing gas flow sensor in the breathing circuit, disruptions in the communication of flow rate data from the ventilator to the nitric oxide delivery system can also occur. In at least some implementations, systems and methods of the present disclosure may detect a discrepancy between any or some of multiple sensors, as described further herein. That is, flow sensing may come from any one or more of the sensors described herein.

In exemplary embodiments, the present disclosure can overcome at least some of the issues described herein by advantageously generating, implementing, and/or utilizing a history of breathing gas flow rate data (e.g. ventilator inspiratory flow information) that is stored within nitric oxide delivery system 100, such as within memory 112. In exemplary embodiments, such historical flow rate data can include one or more of moving average or moving median breathing gas flow rates for a certain period of time, such as the past 5, 10, 15, 20, 30 or 45 seconds, the past 1, 2, 5, 10, 15, 20, 30, 45, 60 minutes, or since the start of the current therapy administration. In at least some implementations, the breathing gas flow rate history is calculated over the past minute (i.e. 60 seconds).

Further, in exemplary embodiments, instead of and/or in addition to moving average or moving median flow rates, in some descriptions the nitric oxide delivery system stores information relating to the breathing gas flow waveform. As with the moving average or moving median breathing gas flow rates, the flow waveform information can be stored for a period of time, such as the past 5, 10, 15, 20, 30 or 45 seconds, the past 1, 2, 5, 10, 15, 20, 30, 45, 60 minutes, or since the start of the current therapy administration. In exemplary embodiments, the waveform itself may be processed into slices or time-identified data points. In at least some implementations, because the data immediately preceding time of the detected disruption may itself be unreliable, the present disclosure may look up a "window" of data having a time ending a set increment before the detected disruption data time, and beginning at the period of set time before the beginning of that window. By way of example, the data may be selected from data selected by any range, e.g., as a window stating 35 seconds before the disruption detection and ending 5 seconds before the disruption detection.

In some implementations, more advanced signal processing techniques may be used for modifying and/or analyzing the historical breathing gas flow rate data. For example, smoothing and/or low-pass filtering, digital finite impulse response filter, and/or digital infinite impulse response filter, may be used to remove outlying flow rate data points.

FIG. 2 illustrates an example where the system controller 111 is configured to receive sensed data via a communication pathway C2 from a sensor located in or at the ventilator 117. As previously noted, the components shown in FIGS. 1-3 disclose similar components with similar reference numbers. Therefore the sake of clarity and brevity, the components common to FIGS. 1-3 are described herein with respect primarily to FIG. 1.

FIG. 3 illustrates an example having both sensors, and where the system controller 111 is configured to receive sensed data via both pathways C1 and C2. When system controller 111 receives data from more than one sensor device, then it can, if desired, monitor each data stream independently to detect if either data stream represents a single respective sensor disruption and/or the system controller 111 may compare the two data streams as part of the process of detecting a disruption in one or more of the sensed data. As further described in various parts of this disclosure, whether receiving information from the ventilator 117 and/or flow sensor 119, system controller 111 can depart from a first mode, which may be referred to as a normal mode, upon detection of a disruption, and can operate in a temporary backup mode, which may also be described as a limp mode, until the disruption has ended, at which time the system controller 111 can return to its normal mode.

Detection of a disruption may be performed by controller 111 which may incorporate or be affiliated therewith, a detection processor configured to detect a disruption of sensed flow rate measurements from any or all associated sensors. In some implementations the detection processor may monitor flow rate data and determine when flow rate data has changed in a way that indicates a disruption, such a termination of data or change in data, digital data error checking. In at least some instances, the detection process may receive and/or detect an indication that a sensor has been disconnected, such as may occur if the injection module is completely or partially disconnected or removed from the system. Upon detection of a disruption, the nitric oxide delivery system utilizes the historical breathing gas flow data for the current delivery of therapeutic gas in the event of disruption or other error in breathing gas flow measurement. For example, in the event of a disruption in breathing gas flow measurement, the nitric oxide delivery system can transition to deliver NO at the set dose based (e.g., in proportion to) the historical breathing gas flow data. In some descriptions, this transition can occur automatically without user intervention.

For nitric oxide delivery systems that have both a breathing gas flow sensor as well as direct communication with a ventilator (e.g. as shown in FIG. 3), if one source of flow data unexpectedly becomes unavailable, the system can seamlessly transition to the other flow data source. If there is a disruption in both data sources or there is a discrepancy between the breathing gas flow information from the two sources, then the nitric oxide delivery system can transition to delivering using the historical flow rate data as described above. If only two data sources (e.g. NO concentration sensor and IM flow sensor) then detection of a disruption can be used based off of these two data sources, for example, when there is loss of data or the flow sensor is reading out of range values.

Once the breathing gas flow information fault/disruption condition is cleared (e.g. once the injector module sensor or entire injector module is serviced or replaced and/or communication with the ventilator is restored; and/or the ventilator sensor is replaced or serviced), the nitric oxide delivery system can seamlessly resume normal proportional NO delivery at the set dose with the current breathing gas flow rate data provided by the breathing gas flow sensor and/or from the ventilator.

Furthermore, in some implementations, in the event that a disruption in breathing gas flow information is detected, an alert (audible alert, visual alert, etc.) may be provided to the user indicating the disruption. For example, a message may appear on the user interface display signaling detection that the breathing gas flow sensor has been disrupted or that communication with the ventilator has been disrupted. For another example, a message or indicator or alarm or the like may be provided to the user indicating detection of a disruption and/or that NO is not being delivered based on historical data, while this condition is present.

Figure 4:
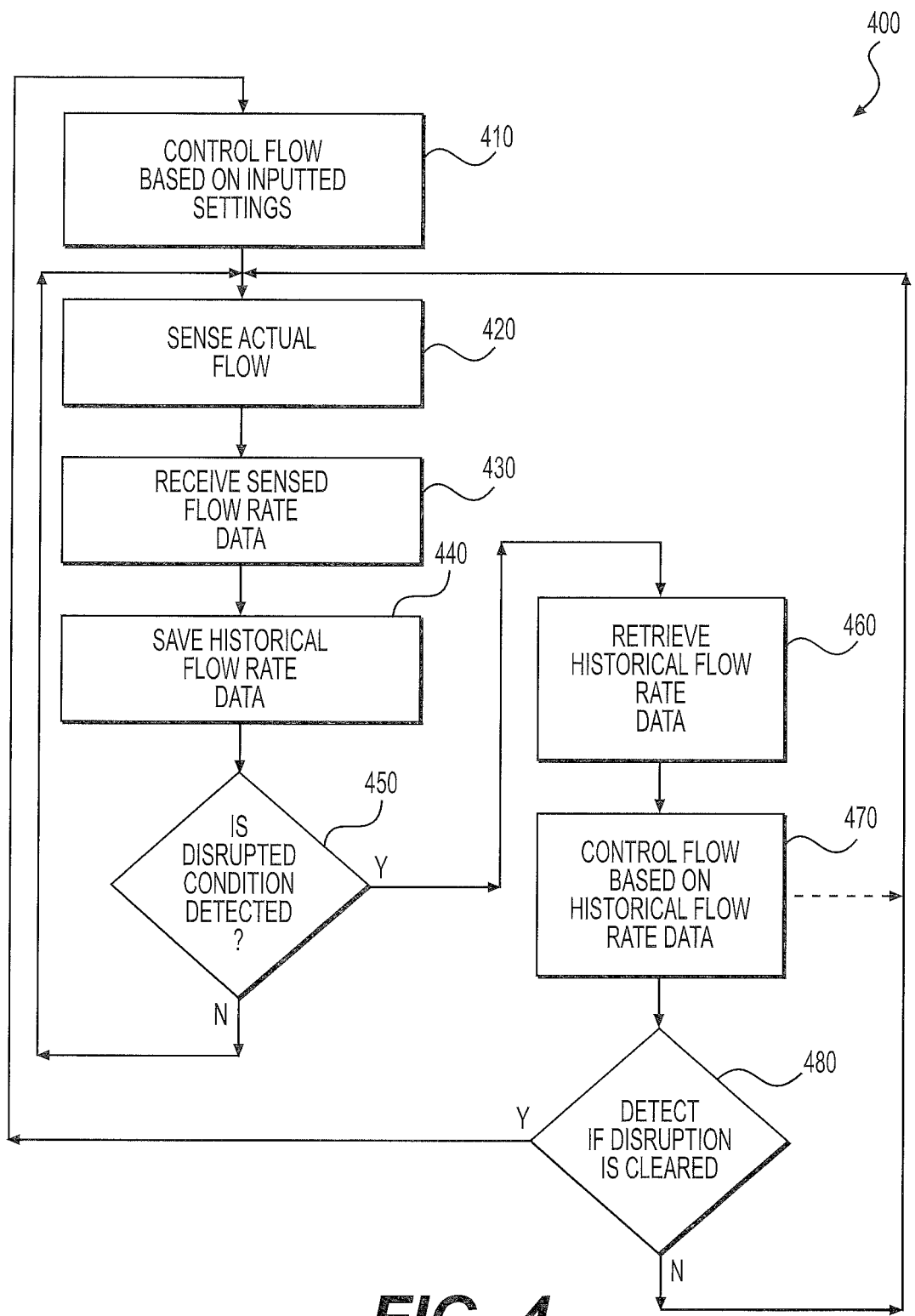
FIG. 4 illustratively depicts an exemplary flow diagram of a method for exemplary NO delivery compensation during disruptions in breathing gas flow measurement.

FIG. 4 illustrates a flow diagram of an exemplary method for compensating for disruptions in breathing gas flow measurement. It will be appreciated that, in some implementations, other flow characteristics besides merely flow rate may also be being sensed or measured by one or more sensors as described herein.

At process 410, the breathing gas flow rate is controlled in a normal mode and provided based on pre-set, desired, input, or otherwise desirable inputted settings. The normal mode settings may be input in some implementations by an operator at user input/display 113, and controlled by controller 111.

At process 420, flow rate data is sensed by one or more sensors in the system. The sensor(s) in some implementations may include a sensor 119 at the injector module and/or a sensor in the ventilator 117, or may be located elsewhere in the overall gas breathing circuit.

At process 430, the controller processes sensed flow rate data from the one or more sensors. The sensor(s) in some implementations may include a sensor 119 at the injector module and/or a sensor in the ventilator 117, or may be located elsewhere in the overall gas breathing circuit. Communication between the sensor(s) and the controller may be for example as shown in dotted lines as C1 and C2 in FIGS. 1-3. Examples of communication include all those described herein, and each may include for example a hardwired and/or wireless communication connection.

At process 440, historical flow rate data is stored in memory for an amount of time. In an example of an implementation, the historical flow rate data is stored over a period in the range from 10 seconds to 5 minutes or breath rate calculated over 1 minute. Could also identify breath cycles and compile an average "breath flow profile". Communication between the sensor(s) and the memory may be for example as shown in dotted lines as C1 and C2 in FIGS. 1-3. Examples of communication include all those described herein, and each may include for example a hardwired and/or wireless communication connection. The controller and memory may be arranged in any order, and may be arranged in a single module.

At process 450, the controller 111 checks or detects whether a disruption (also referred to as a fault) condition of a sensor is detected by analysis of the received flow rate data. The analysis of the received flow rate data either analog or digital may occur via the controller 111. If no disruption is detected, then the system continues normal operation. The disruption may be a total lack of data or other fault condition, or may be any change of data indicative of irregularity of the data, or fault of the system. For example, the disruption may be any of those described herein, or other disruptions, including in some implementations, the disconnection of the injector module, a lack of matching data determined between two sensors, an out-of-expected band flow rate data reading, etc. An example of an out-of-expected band flow rate data reading may be, 10 ms of data loss or out of range flow readings or 10 seconds of miss-matched flow readings.

At process 460, when a disruption is detected at process 450, controller 111 retrieves historical flow rate data from memory 112. The controller and memory may be arranged in any order, and may be arranged in a single module. In some implementations, the historical flow rate data may be a selected time window, which as described herein, may be a fixed time window of historical data during a time window before the detected disruption. The time window, in some implementations, may end immediately before the detected disruption time, or may end a period before the detected disruption time. For example, a reference disruption time may be 1 minute moving average flow rate calculated up to 10 seconds before the point of signal loss, out of range signal, or signal disagreement.

At process 470, flow control is based on historical flow rate data. In some implementations, the controller 111 will use as its operating parameters the historical flow rate data from the memory 112, to provide a second mode, which may be referred to as a Historical Proportional Gas Delivery backup mode, and/or also may also be referred to as an Injector Failure Temporary Backup Mode. As described herein, the temporary backup mode provides continued operation of the overall system, so that gas continues to be provided and controlled by the controller 111, even after some disruption of normal sensing of gas flow rate has been detected.

At process 480, if the user so indicates, or the controller determines, that the disruption is no longer occurring, and/or has been cleared (e.g. by the user indicating a replacement or service of the sensor, and/or the system detecting repair or replacement of a sensor), then the system returns to normal mode, using initial settings from the normal mode, such as for example the parameters inputted at process 410. As an example, the disruption may be considered cleared after the volumetric flow rate is determined to be within 20% of the historical average. When digital communication signals are established with CRC messages. With analog signals the disruption may be considered cleared when the flow rate is within expected ADC count limits for either flow or temperature reporting.

Figure 5:
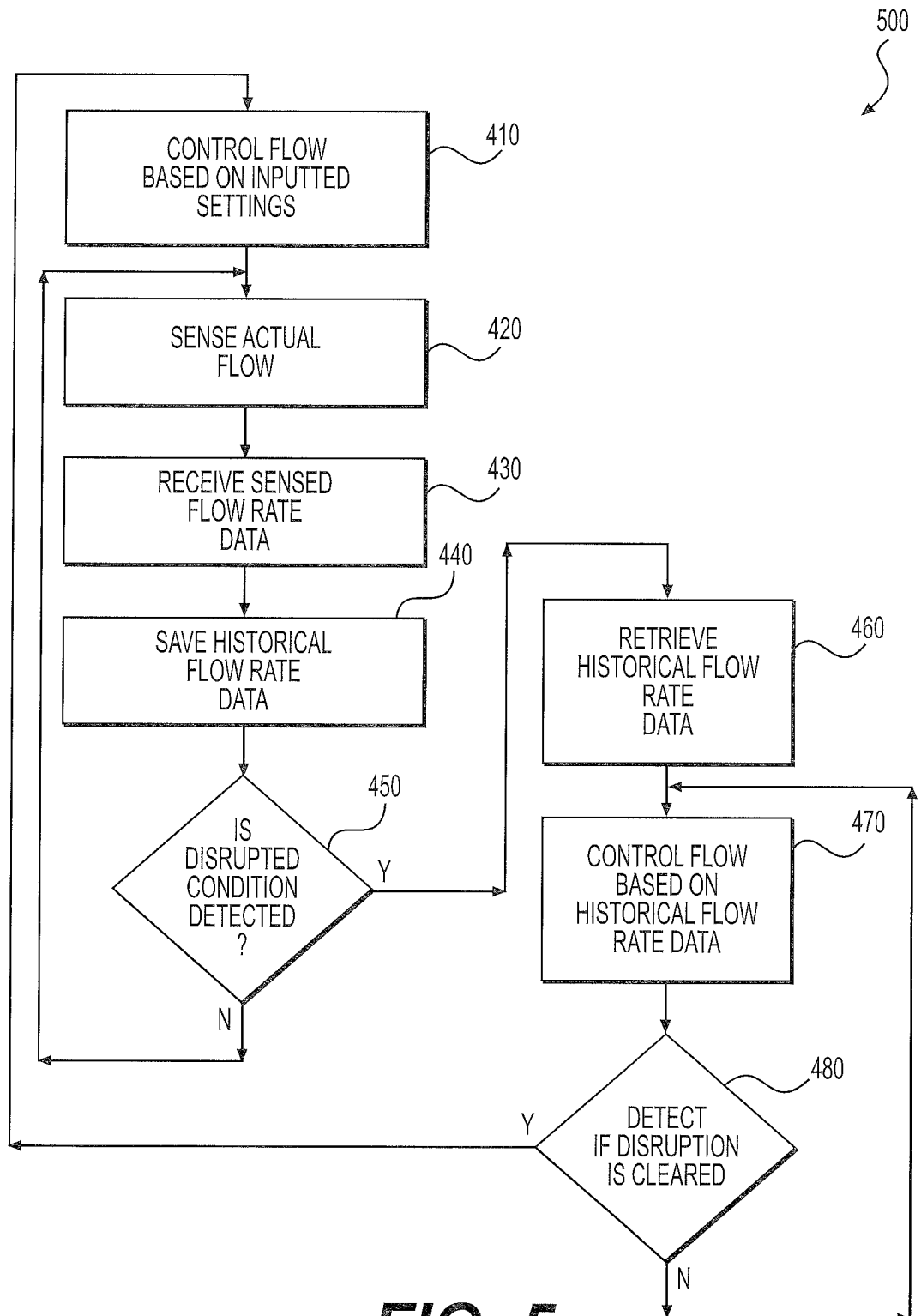
FIG. 5 illustratively depicts a flow diagram variation of the method shown in FIG. 4.

FIG. 5 is a flow diagram similar to FIG. 4, with similar reference numbers but showing a variation of an implementation. In the implementation 500 of FIG. 5, at process 480 when the disruption is not detected to be cleared, then the flow is controlled based on historical flow rate data at process 470.

The description herein utilizes the term gas flow rate data (e.g., volumetric flow rate, mass flow rate, etc.). However, in some implementations, this term can also refer to additional or other information besides or in addition to flow rate, such as any information related to delivery of therapeutic gas such as, for example, measurements of gas ratios, gas concentrations, etc. The system may also track historical NO flow sensor reading data, or historical control system commanded NO flow rate.

In some implementations, the user can adjust the dose of therapeutic gas when the system is in the backup mode. Historical data may continue to be referenced to calculate the desired NO flow rate for the new set dose. When in the backup mode, the historical average flow rate being used may be displayed on an information display screen associated with the device. A GUI or other control interfaces may be provided, for example, it may be provided to the user to change various settings of a ventilator or other components while the backup mode is in progress. Also, instead of, or in addition to using historical measured flow rates, the controller may utilize a record in memory of historical commanded (or input controlled) flow rates coming from the controller.

The foregoing detailed descriptions are presented to enable any person skilled in the art to make and use the disclosed subject matter. For purposes of explanation, specific nomenclature is set forth to provide a thorough understanding. However, it will be apparent to one skilled in the art that these specific details are not required to practice the disclosed subject matter. Descriptions of specific applications are provided only as representative examples. Various modifications to the disclosed implementations will be readily apparent to one skilled in the art, and the general principles defined herein may be applied to other implementations and applications without departing from the scope of this disclosure. The sequences of operations described herein are merely examples, and the sequences of operations are not limited to those set forth herein, but may be changed as will be apparent to one of ordinary skill in the art, with the exception of operations necessarily occurring in a certain order. Also, description of functions and constructions that are well known to one of ordinary skill in the art may be omitted for increased clarity and conciseness. This disclosure is not intended to be limited to the implementations shown, but is to be accorded the widest possible scope consistent with the principles and features disclosed herein.

It will be apparent to those skilled in the art that various modifications and variations can be made to the methods and systems of the present description without departing from the spirit and scope of the description. Thus, it is intended that the present description include modifications and variations that are within the scope of the appended claims and their equivalents.

It will be understood that any of the steps described can be rearranged, separated, and/or combined without deviated from the scope of the invention. For ease, steps are, at times, presented sequentially. This is merely for ease and is in no way meant to be a limitation. Further, it will be understood that any of the elements and/or embodiments of the invention described can be rearranged, separated, and/or combined without deviated from the scope of the invention. For ease, various elements are described, at times, separately. This is merely for ease and is in no way meant to be a limitation.

The separation of various system components in the examples described above should not be understood as requiring such separation in all examples, and it should be understood that the described components and systems can generally be integrated together in a single packaged into multiple systems and/or multiple components. It is understood that various modifications may be made therein and that the subject matter disclosed herein may be implemented in various forms and examples, and that the teachings may be applied in numerous applications, only some of which have been described herein. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A nitric oxide gas delivery apparatus for use with a ventilator, the apparatus comprising:
    an injector module operable to be placed in fluid communication with a breathing circuit affiliated with the ventilator, the injector module comprising:
        a breathing gas flow inlet;
        a nitric oxide (NO) flow inlet; and
        a combined breathing gas and NO flow outlet operable to provide a combined flow of breathing gas and NO to a patient, in need thereof;
    a breathing gas flow sensor configured to sense breathing gas flow rate;
    one or more NO flow sensors operable to measure the flow of NO; and
    a controller comprising:
        a memory operable to track and store historical NO flow rate data by the one or more NO flow sensors; and
        a processor operable to calculate a historical average NO flow rate from the historical NO flow rate data in a first mode and detect a disruption of breathing gas flow rate data from the breathing gas flow sensor,
        wherein upon detection of the disruption in breathing gas flow rate data, the controller operates in a backup mode to control a delivery flow rate of the NO based on the historical average NO flow rate.

2. The apparatus of claim 1, wherein the controller operating in backup mode controls the delivery flow rate of the NO at the historical average NO flow rate.

3. The apparatus of claim 1, wherein the historical average NO flow rate is referenced to calculate a desired NO flow rate for a new set dose of NO.

4. The apparatus of claim 1, further comprising a user input, wherein when the controller is operating in backup mode, a record in the memory from the user input controls the delivery flow rate of the NO.

5. The apparatus of claim 1, further comprising a display, wherein when the controller is operating in the backup mode, the historical average NO flow rate is displayed on the display.

6. The apparatus of claim 1, further comprising a control valve operable to regulate flow of the NO through a conduit to the injector module.

7. The apparatus of claim 6, wherein the one or more NO flow sensors are located upstream from the control valve and/or the conduit, and wherein the one or more NO flow sensors are operable to measure the flow of NO through the NO flow inlet into the injector module.

8. The apparatus of claim 6, wherein the one or more NO flow sensors are located downstream from the control valve and/or the conduit, and wherein the one or more NO flow sensors are operable to measure the flow of NO through the NO flow inlet into the injector module.

9. The apparatus of claim 1, wherein the controller is operable to automatically return to the first mode upon detection that the disruption has ended and/or that the breathing gas flow sensor has been at least one of reconnected, replaced, and/or serviced.

10. The apparatus of claim 1, wherein the controller is configured to automatically resume delivery of a flow of NO based on the first mode, upon detection and/or input that the breathing gas flow sensor has been at least one of reconnected, replaced, and/or serviced.

11. The apparatus of claim 1, wherein the historical NO flow rate data is stored over a period in the range from 10 seconds to 5 minutes.

12. The apparatus of claim 1, wherein the sensed breathing gas flow rate data is received from the injector module and/or the ventilator.

13. The apparatus of claim 1, wherein the sensed breathing gas flow rate data comprises first breathing gas flow rate data and second breathing gas flow rate data, and wherein the first breathing gas flow rate data is received from the injector module and/or the second breathing gas flow rate data is received from the ventilator.

14. The apparatus of claim 13, wherein the controller compares respective flow rate data from the first breathing gas flow rate data with the second breathing gas flow rate data.

15. The apparatus of claim 1, wherein the controller is further operable to utilize at least one of data smoothing and/or low-pass filtering to remove outlying stored flow data points.

16. A method for delivery of nitric oxide (NO) gas to a patient, the method comprising:
    controlling, via a controller, a NO flow to a patient in a first mode;
    receiving, via a breathing gas sensor, sensed flow rate of breathing gas flow;
    receiving, via one or more NO flow sensors, measured flow rate of NO flow;
    storing in a memory historical NO flow rate data related to the received NO flow rate by the one or more NO sensors;
    calculating, via a processor, a historical average NO flow rate from the historical NO flow rate data in the first mode;
    detecting a disruption of the sensed breathing gas flow rate data from the breathing gas sensor; and
    controlling, via the controller, the NO flow in a backup mode instead of the first mode, based on the historical average NO flow rate.

17. The method of claim 16, further comprising displaying the historical average NO flow rate on a display when the controller is operating in the backup mode.

18. The method of claim 16, wherein when the controller is operating in backup mode, a record in the memory from a user input controls the flow rate of the NO.

19. The method of claim 16, wherein storing the historical NO flow rate data includes storing the historical NO flow rate data over a period in the range from 10 seconds to 5 minutes.

20. The method of claim 16, further comprising:
returning to the first mode when a discontinuance of the disruption is detected.

21. The method of claim 20, wherein:
receiving the received breathing gas flow rate data includes receiving a first breathing gas flow rate data and a second breathing gas flow rate data, and
detecting the disruption includes detecting the disruption by comparing respective flow rate data between the first and second breathing gas flow rate data.

* * * * *